United States Patent [19]

Dickinson et al.

[11] 4,039,550

[45] Aug. 2, 1977

[54] LOWER-ALKYL (5-SUBSTITUTED-2-PYRIDYL)CARBAMODITHIOATES

[75] Inventors: William B. Dickinson, Albany; Marcia P. Vaupotic, Sand Lake, both of N.Y.

[73] Assignee: Sterling Drug Inc., New York, N.Y.

[21] Appl. No.: 708,903

[22] Filed: July 26, 1976

[51] Int. Cl.$^2$ .......................................... C07D 213/52
[52] U.S. Cl. ........................... 260/294.8 E; 424/263
[58] Field of Search ................................ 260/294.8 E

[56] References Cited

U.S. PATENT DOCUMENTS 2,789,114   4/1957   Fischback et al. ............ 260/294.8 E

OTHER PUBLICATIONS

Knott, Chem. Abstracts, vol. 53, (2), pp. 944–946, Jan. 25, 1959.
Knott, Chem. Abstracts, vol. 51, (1), pp. 408–410; Jan. 10, 1957.
Chem. Abstracts, Seventh Collective Index, Subjects Ps–Sn, p. 19220–S, vols. 56–65 (1962–1966).

*Primary Examiner*—Alan L. Rotman
*Attorney, Agent, or Firm*—William G. Webb; B. Woodrow Wyatt

[57] ABSTRACT

Lower-alkyl (5-$R_5$-2-pyridyl)carbamodithioates, prepared by reaction of a 5-$R_5$-2-aminopyridine with carbon disulfide in the presence of a tri-lower-alkylamine and reaction of the resulting tri-lower-alkyl ammonium (5-$R_5$-2-pyridyl)carbamodithioate with a lower-alkyl halide, where $R_5$ is chloro, lower-alkyl or di-lower-alkylamino, are useful as anthelmintic agents.

4 Claims, No Drawings

LOWER-ALKYL (5-SUBSTITUTED-2-PYRIDYL)CARBAMODITHIOATES

BACKGROUND OF THE INVENTION a. Field of the Invention

This invention relates to lower-alkyl (5-$R_5$-2-pyridyl)-carbamodithioates, where $R_5$ is chloro, lower-alkyl or di-lower-alkylamino, useful as anthelmintic agents.

b. Description of the Prior Art

Knott, U.S. Pat. No. 2,839,403 (patented June 17, 1958) discloses methyl (2-pyridyl)carbamodithioate; ethyl (2-pyridyl)carbamodithioate; methyl (3-pyridyl)-carbamodithioate; methyl (6-methyl-2-pyridyl)carbamodithioate; methyl (4-methyl-2-pyridyl)carbamodithioate and methyl (4-pyridyl)carbamodithioate, all useful as intermediates for the preparation of merocyanine dyes. Ethyl (2-pyridyl)-carbamodithioate is also disclosed by Foye et al., J. Am. Pharm. Assoc. 47, 556–558 (1958) who also teach that the compound is active as an anti-bacterial agent.

SUMMARY OF THE INVENTION

This invention relates, in a composition of matter aspect, to lower-alkyl (5-$R_5$-2-pyridyl)dithiocarbamates where $R_5$ is chloro, lower-alkyl or di-lower-alkylamino.

In a process aspect, the invention relates to a process for preparing the said lower-alkyl (5-$R_5$-2-pyridyl)-dithiocarbamates which comprises reacting a 5-$R_5$-2-aminopyridine with carbon disulfide in the presence of a tri-lower-alkylamine and reacting the resulting tri-lower-alkylammonium (5-$R_5$-2-pyridyl)dithiocarbamate with a lower-alkyl halide.

DETAILED DESCRIPTION INCLUSIVE OF THE PREFERRED EMBODIMENTS

More specifically, this invention relates to lower-alkyl (5-$R_5$-2-pyridyl)dithiocarbamates having the formula:

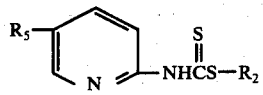

I where $R_2$ is lower-alkyl and $R_5$ is chloro, lower-alkyl or di-lower-alkylamino.

As used herein, the term lower-alkyl means a saturated, monovalent, aliphatic, non-tertiary, hydrocarbon radical, including a straight or branched-chain radical, of from one to four carbon atoms, as illustrated by methyl, ethyl, propyl, isopropyl, butyl, sec.-butyl and isobutyl.

The compounds of formula I are prepared by reacting a 5-$R_5$-2-aminopyridine having the formula II with carbon disulfide in the presence of a tri-lower-alkylamine and reacting the resulting tri-lower-alkylammonium (5-$R_5$-2-pyridyl)dithiocarbamate with a lower-alkyl halide, $R_2X$. The process is represented by the following reaction sequence:

where $R_2$ and $R_5$ have the meanings given above, R is lower-alkyl and X is halogen. Both the reaction of the 5-$R_5$-2-aminopyridine with carbon disulfide in the presence of a tri-lower-alkylamine and the reaction of the resulting tri-lower-alkylammonium (5-$R_5$-2-pyridyl)dithiocarbamate of formula III with a lower-alkyl halide are preferably carried out in an organic solvent inert under the reaction conditions. Suitable solvents are acetonitrile, chloroform, a lower-alkanol such as methanol, benzene, dimethylformamide or tetrahydrofuran. A preferred solvent for the first reaction is acetonitrile, and a preferred solvent for the second reaction is a lower-alkanol, for example methanol.

The 5-$R_5$-2-aminopyridines of formula II and the lower-alkyl halides, $R_2X$, are generally known compounds.

In standard biological test procedures, the compounds of formula I have been found to possess anthelmintic activity and are useful as anthelmintic agents. Anthelmintic activity was determined in mice against one species of roundworm (*Nematospiroides dubius*), one species of pinworm (*Syphacia obvelata*) and one species of tapeworm (*Hymenolepis nana*). The various test procedures used are described as follows: Swiss mice weighing approximately 20 grams were infected with approximately 20 larvae of *N. dubius* which were administered in 10% gelatin via stomach tube. For screening purposes, compounds, made up in 10% gelatin, were administered via stomach tube in equally divided daily doses for four consecutive days beginning fourteen days after infection. Four days after the final medication, the animals were sacrificed and examined for the presence of worms. efficacy against *N. dubius* was judged on the basis of percent worm reduction compared to control non-medicated mice. In addition, for the purpose of evaluation, the compounds were administered orally to a series of animals at graded doses, each animal receiving a single dose, and the results against *N. dubius* expressed in terms of an Effective Dose$_{50}$ (ED$_{50}$), the ED$_{50}$ representing the dose necessary to remove 50% of the worm burden.

The same test procedures described above were used to assess the effectiveness of the compounds against *S. obvelata*, a naturally occurring pinworm infection in Swiss mice. Efficacy was judged by the percent of mice cleared of the infection compared to non-medicated control mice.

In tests against the tapeworm, *H. nana*, Swiss mice weighing approximately 20 grams were infected with approximately 12,000 ova of *H. nana* administered in 10% gelatin via stomach tube. The test compounds, made up in 10% gelatin, were administered via stomach tube in equally divided doses daily for four consecutive days beginning twelve days after infection. Four days after the final medication, the animals were sacrificed and examined for the presence of worms. Efficacy was judged by the percent of mice cleared compared to non-medicated control mice.

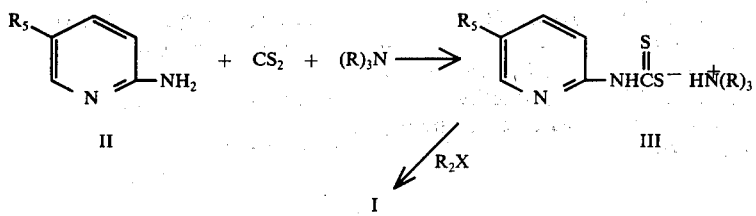

The lower-alkyl (5-$R_5$-2-pyridyl)carbamodithioates of formula I were found to reduce or eliminate the helminth burden from infected mice when administered in the dose range of from 2 to 200 mg./kg. The compounds are preferably administered orally, and the amount of a particular compound to be administered, either by itself or as the essential active ingredient in a formulation, will range from 2 to about 200 mg./kg. The number of doses administered range from one to two per day for from one to five consecutive days, depending on the severity of the helminth infestation.

The actual determination of the numerical biological data definitive for a particular compound of formula I is readily determined by standard test procedures by technicians versed in pharmacological test procedures, without the need for any extensive experimentation.

The compounds of formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

A mixture of 102 g. (0.8 mole) of 5-chloro-2-aminopyridine [Friedrich et al., Pharmazie, 19 (10), 677–678 (1964)], 20 ml. of acetonitrile, 161 g. (1.6 mole) of triethylamine and 64 g. (0.84 mole) of carbon disulfide was stirred at ambient temperature for five hours. After standing for about forty-eight hours, the solid which had separated was collected and dried to give 109.2 g. of tri-ethylammonium (5-chloro-2-pyridyl)carbamodithioate which was suspended in 700 ml. of methanol and treated slowly with a solution of 50 g. (0.36 mole) of methyl iodide in 100 ml. of methanol. The mixture was stirred for three hours and the solid precipitate was collected and dried to give 23.5 g. of methyl (5-chloro-2-pyridyl)carbamodithioate, m.p. 164°–165° C.

Anal. Calcd. for $C_7H_7ClN_2S_2$: N, 12.81; S, 29.32. Found: N, 12.89; S, 29.34.

EXAMPLE 2

Following a procedure similar to that described in Example 1 above, 43.2 g. (0.4 mole) of 5-methyl-2-aminopyridine [Dorie et al., Org. Magn. Resonance, 3 (6), 661–677 (1971)] was reacted with 32.0 g. (0.42 mole) of carbon disulfide and 80.8 g. (0.8 mole) of triethylamine in 36 ml. of acetonitrile, and 14.25 g. (0.05 mole) of the resulting 106.3 g. of triethylammonium (5-methyl-2-pyridyl)carbamodithioate (m.p. 80°–84° C.) was reacted with 7.8 g. (0.055 mole) of methyl iodide in 55 ml. of chloroform. There was thus obtained 11.85 g. of methyl (5-methyl-2-pyridyl)carbamodithioate, m.p. 105°–117° C. which, on recrystallization from acetonitrile, afforded 8.1 g. of pure material having m.p. 118.5°–122° C.

Anal. Calcd. for $C_8H_{10}N_2S_2$: N, 14.13; S, 32.34. Found: N, 14.50; S, 31.98.

EXAMPLE 2A

Following a procedure similar to that described in Example 1 above, 5-ethyl-2-aminopyridine [Ban et al., Chem. Ind. (London) 1964 (17), 710–711] is reacted with carbon disulfide and triethylamine in acetonitrile and the resulting triethylammonium (5-ethyl-2-pyridyl)carbamodithioate rected with ethyl iodide to give ethyl (5-ethyl-2-pyridyl)carbamodithioate.

EXAMPLE 3

Following a procedure similar to that described in Example 1, 0.12 mole of 5-dimethylamino-2-aminopyridine [Fox, J. Chem. Soc. 1, 1973, 68–69, Perkin Trans.] was reacted with 15 ml. of carbon disulfide and 30 ml. of triethylamine in 20 ml. of acetonitrile and the resulting triethylammonium (5-dimethylamino-2-pyridyl)carbamodithioate (22 g.) was reacted with 10 g. of methyl iodide in 200 ml. of methanol to give 10 g. of methyl (5-dimethylamino-2-pyridyl)carbamodithioate, m.p. 124°–125° C.

Anal. Calcd. for $C_9H_{13}N_3S_2$: N, 18.48; S, 28.21. Found: N, 18.40; S, 28.30.

BIOLOGICAL TEST RESULTS

Data obtained in anthelmintic screening tests against the helminth infections, *N. dubius* (a), *H. nana* (b) and *S. obvelata* (c), are given in the table below. Results are expressed in terms of the percent of animals cleared at a standard dose of 200 mg./kg./day (p.o.) for four days; as percent of animals cleared at a single dose (S.D.) of 25 mg./kg.; or as an $ED_{50}$ on single dose administration ($ED_{50}$) against *N. dubius*.

| Example | % Cleared/200 mg./kg. (a) | (b) | (c) | S.D. | $ED_{50}$ |
|---|---|---|---|---|---|
| 1 | 100 | 80 | 40 | — | 2.0±0.917 |
| 2 | 100 | 30 | 30 | — | 7.75±3.54 |
| 3 | 100 | 0 | 0 | 64.5 | — |

We claim:

1. A compound having the formula:

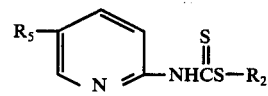

where $R_2$ is lower-alkyl and $R_5$ is chloro.

2. A compound having the formula:

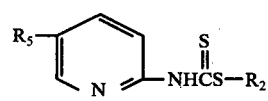

where $R_2$ is lower-alkyl and $R_5$ is di-lower-alkylamino.

3. Methyl (5-chloro-2-pyridyl)carbamodithioate according to claim 1.

4. Methyl (5-dimethylamino-2-pyridyl)carbamodithioate according to claim 2.

* * * * *